US009140681B2

(12) United States Patent
Smith et al.

(10) Patent No.: US 9,140,681 B2
(45) Date of Patent: Sep. 22, 2015

(54) METHOD FOR QUANTITATIVELY DETERMINING EYELASH CLUMPING

(71) Applicant: The Procter & Gamble Company, Cincinnati, OH (US)

(72) Inventors: Charles Robert Smith, Swindon (GB); Jennifer Clare Hodgetts, Addlestone (GB)

(73) Assignee: The Procter & Gamble Company, Cincinnati, OH (US)

( * ) Notice: Subject to any disclaimer, the term of this patent is extended or adjusted under 35 U.S.C. 154(b) by 174 days.

(21) Appl. No.: 13/894,665

(22) Filed: May 15, 2013

(65) Prior Publication Data

US 2013/0308823 A1 Nov. 21, 2013

Related U.S. Application Data (60) Provisional application No. 61/646,961, filed on May 15, 2012.

(51) Int. Cl.
*G06K 9/00* (2006.01)
*G01N 33/483* (2006.01)
*A45D 44/00* (2006.01)
*G01N 21/84* (2006.01)
*G01N 21/898* (2006.01)
*G01N 21/94* (2006.01)

(52) U.S. Cl.
CPC ............ *G01N 33/4833* (2013.01); *A45D 44/00* (2013.01); *G01N 21/84* (2013.01); *G01N 21/8983* (2013.01); *G01N 21/94* (2013.01); *G06K 9/00604* (2013.01); *A45D 2044/007* (2013.01)

(58) Field of Classification Search
None
See application file for complete search history.

(56) References Cited

U.S. PATENT DOCUMENTS

| 2,458,063 | A | * | 1/1949 | Dulberg | 132/314 |
|---|---|---|---|---|---|
| 2,831,854 | A | | 4/1958 | Tucker | |
| 2,900,306 | A | | 8/1959 | Slater | |
| 3,255,082 | A | | 6/1966 | Barton | |
| 3,677,271 | A | | 7/1972 | Luciano | |
| 3,690,777 | A | | 9/1972 | Costa | |
| 3,739,789 | A | | 6/1973 | Cataneo | |
| 3,802,841 | A | | 4/1974 | Robin | |
| 3,963,699 | A | | 6/1976 | Rizzi et al. | |
| 4,005,195 | A | | 1/1977 | Jandacek | |
| 4,005,196 | A | | 1/1977 | Jandacek et al. | |
| 4,126,679 | A | | 11/1978 | Davy et al. | |
| 4,137,306 | A | | 1/1979 | Rubino et al. | |

(Continued)

FOREIGN PATENT DOCUMENTS

| CN | 300856708 | 12/2008 |
|---|---|---|
| CN | 300856709 | 12/2008 |

(Continued)

OTHER PUBLICATIONS

Avon, Avon Colour, in a Blink Eye Shadow and Liner, date published Mar. 2007; www.gnpd.com, 2 pages.

(Continued)

*Primary Examiner* — Nancy Bitar (57) ABSTRACT

A method for quantifying clumping in fibrous materials is disclosed herein. In some examples, the method may be utilized for quantifying clumping in keratinous materials such as eyelashes when a composition such as mascara is applied thereto.

18 Claims, 9 Drawing Sheets

(56) References Cited

U.S. PATENT DOCUMENTS

| | | | |
|---|---|---|---|
| 4,151,272 A | 4/1979 | Geary et al. | |
| 4,154,816 A | 5/1979 | Roehl et al. | |
| D252,911 S | 9/1979 | Levy | |
| 4,202,879 A | 5/1980 | Shelton | |
| 4,226,889 A | 10/1980 | Yuhas | |
| 4,228,277 A | 10/1980 | Landoll | |
| 4,229,432 A | 10/1980 | Geria | |
| 4,280,994 A | 7/1981 | Turney | |
| 4,322,400 A | 3/1982 | Yuhas | |
| 4,336,246 A | 6/1982 | Leon-Pekarek | |
| 4,346,079 A | 8/1982 | Roehl | |
| 4,383,988 A | 5/1983 | Teng et al. | |
| D277,324 S | 1/1985 | Davey | |
| 4,517,360 A | 5/1985 | Volpenhein | |
| 4,518,772 A | 5/1985 | Volpenhein | |
| 4,725,432 A | 2/1988 | May | |
| 4,759,924 A | 7/1988 | Luebbe et al. | |
| 4,797,300 A | 1/1989 | Jandacek et al. | |
| 4,816,261 A | 3/1989 | Luebbe et al. | |
| 4,886,080 A | 12/1989 | Cole | |
| 4,932,802 A | 6/1990 | Cantone | |
| 4,980,155 A | 12/1990 | Shah et al. | |
| 5,017,398 A | 5/1991 | Jandacek et al. | |
| 5,019,375 A | 5/1991 | Tanner et al. | |
| 5,040,914 A | 8/1991 | Fitjer | |
| 5,097,853 A | 3/1992 | Nehashi | |
| 5,104,646 A | 4/1992 | Bolich, Jr. et al. | |
| RE33,996 E | 7/1992 | Jandacek | |
| 5,165,917 A | 11/1992 | Zabotto | |
| 5,193,918 A | 3/1993 | Lohrmann et al. | |
| 5,306,514 A | 4/1994 | Letton et al. | |
| 5,306,515 A | 4/1994 | Letton et al. | |
| 5,306,516 A | 4/1994 | Letton et al. | |
| RE34,617 E | 5/1994 | Jandacek et al. | |
| 5,376,231 A | 12/1994 | Matsumoto et al. | |
| 5,389,363 A | 2/1995 | Snyder | |
| D360,486 S | 7/1995 | Schultz | |
| 5,490,529 A | 2/1996 | Fitjer | |
| 5,794,632 A * | 8/1998 | Gueret | 132/317 |
| 5,832,942 A | 11/1998 | Gutberlet | |
| 5,866,434 A | 2/1999 | Massey et al. | |
| D422,748 S | 4/2000 | Lang | |
| 6,071,503 A | 6/2000 | Drechsler et al. | |
| 6,074,654 A | 6/2000 | Drechsler et al. | |
| 6,080,687 A | 6/2000 | Ishwarlal | |
| 6,139,823 A | 10/2000 | Drechsler et al. | |
| 6,200,045 B1 | 3/2001 | Hahn et al. | |
| 6,203,814 B1 | 3/2001 | Fisher et al. | |
| 6,241,408 B1 | 6/2001 | Lang | |
| 6,267,951 B1 | 7/2001 | Shah et al. | |
| 6,303,105 B1 | 10/2001 | Shah et al. | |
| D450,888 S | 11/2001 | Breidenbach et al. | |
| 6,340,466 B1 | 1/2002 | Drechsler et al. | |
| D453,588 S | 2/2002 | Breidenbach et al. | |
| D453,589 S | 2/2002 | Breidenbach et al. | |
| 6,450,179 B2 | 9/2002 | Bengis | |
| 6,464,418 B1 | 10/2002 | Visser | |
| 6,488,427 B1 | 12/2002 | Breidenbach et al. | |
| 6,491,902 B2 | 12/2002 | Shefer et al. | |
| 6,500,446 B1 | 12/2002 | Derrieu et al. | |
| 6,502,584 B1 * | 1/2003 | Fordham | 132/218 |
| D474,341 S | 5/2003 | Cantone et al. | |
| 6,612,764 B2 | 9/2003 | Dumler | |
| 6,637,963 B2 * | 10/2003 | Huang | 401/19 |
| D482,284 S | 11/2003 | Cantone et al. | |
| 6,682,242 B1 | 1/2004 | Montoli | |
| D497,455 S | 10/2004 | Lee | |
| 6,811,770 B2 | 11/2004 | Ferrari et al. | |
| 6,979,440 B2 | 12/2005 | Shefer et al. | |
| 6,985,879 B2 | 1/2006 | Walker et al. | |
| 7,077,591 B2 | 7/2006 | Gueret | |
| D530,857 S | 10/2006 | Black | |
| 7,168,875 B1 | 1/2007 | Zhang | |
| 7,175,359 B2 | 2/2007 | Zhang | |
| 7,186,274 B2 | 3/2007 | Vic et al. | |
| D542,978 S | 5/2007 | Bortolotti | |
| 7,210,870 B2 | 5/2007 | Breidenbach et al. | |
| 7,226,227 B2 * | 6/2007 | Gueret | 401/18 |
| 7,241,835 B2 | 7/2007 | O'Brien et al. | |
| 7,276,088 B2 | 10/2007 | Huang et al. | |
| D561,390 S | 2/2008 | Sugawara | |
| D566,335 S | 4/2008 | Althoff et al. | |
| D566,337 S | 4/2008 | Althoff et al. | |
| D574,154 S | 8/2008 | Dumler et al. | |
| D574,155 S | 8/2008 | Dumler et al. | |
| D578,770 S | 10/2008 | Berhault | |
| D579,208 S | 10/2008 | Berhault | |
| 7,438,953 B2 | 10/2008 | Kotov et al. | |
| D581,169 S | 11/2008 | Berhault | |
| D583,506 S | 12/2008 | Justice | |
| D585,600 S | 1/2009 | Althoff et al. | |
| 7,473,045 B2 | 1/2009 | Dumler | |
| D592,858 S | 5/2009 | Berhault | |
| D593,330 S | 6/2009 | Berhault | |
| D593,331 S | 6/2009 | Berhault | |
| D598,657 S | 8/2009 | Berhault | |
| D600,921 S | 9/2009 | Berhault | |
| D600,922 S | 9/2009 | Berhault | |
| D600,923 S | 9/2009 | Berhault | |
| 7,632,489 B2 | 12/2009 | Wyatt et al. | |
| D615,419 S | 5/2010 | Owen | |
| 7,780,875 B2 | 8/2010 | Asgari | |
| 7,842,285 B2 | 11/2010 | Lu et al. | |
| 7,856,806 B1 | 12/2010 | Chasman et al. | |
| D634,127 S | 3/2011 | Burgess et al. | |
| D634,478 S | 3/2011 | Kolas et al. | |
| D636,940 S | 4/2011 | Acierto et al. | |
| D642,805 S | 8/2011 | Burgess et al. | |
| 7,993,661 B2 | 8/2011 | Arnaud et al. | |
| D653,398 S | 1/2012 | Acierto et al. | |
| 8,096,306 B2 | 1/2012 | Malvar et al. | |
| D654,626 S | 2/2012 | Kolas et al. | |
| 8,168,095 B2 | 5/2012 | Alberius et al. | |
| 8,298,494 B2 | 10/2012 | Komiya et al. | |
| 8,323,628 B2 | 12/2012 | Atis | |
| 8,329,147 B2 | 12/2012 | Ansmann et al. | |
| 8,336,560 B2 | 12/2012 | Dumler et al. | |
| 8,444,930 B2 | 5/2013 | Komiya et al. | |
| 2001/0051168 A1 | 12/2001 | Ramin et al. | |
| 2002/0071707 A1 * | 6/2002 | Breidenbach et al. | 401/171 |
| 2002/0076390 A1 | 6/2002 | Kantner et al. | |
| 2002/0083954 A1 * | 7/2002 | Gavney, Jr. | 132/297 |
| 2002/0185148 A1 | 12/2002 | Bengis | |
| 2002/0190336 A1 | 12/2002 | Shimizu et al. | |
| 2003/0041870 A1 | 3/2003 | Su | |
| 2003/0086741 A1 | 5/2003 | Kim | |
| 2003/0095935 A1 | 5/2003 | Chaiyawat et al. | |
| 2003/0143181 A1 | 7/2003 | Hensen et al. | |
| 2004/0105828 A1 | 6/2004 | Chaiyawat et al. | |
| 2004/0115232 A1 | 6/2004 | Giroud et al. | |
| 2004/0126303 A1 | 7/2004 | Hwang | |
| 2004/0190974 A1 * | 9/2004 | Cantone et al. | 401/25 |
| 2004/0228890 A1 | 11/2004 | Blin et al. | |
| 2004/0234564 A1 | 11/2004 | Blin et al. | |
| 2005/0095213 A1 | 5/2005 | Blin et al. | |
| 2005/0176598 A1 | 8/2005 | Bergquist et al. | |
| 2005/0186167 A1 | 8/2005 | Ueda et al. | |
| 2005/0276779 A1 | 12/2005 | Blin | |
| 2006/0029560 A1 | 2/2006 | Blin | |
| 2006/0067783 A1 | 3/2006 | Tsaur | |
| 2006/0127339 A1 | 6/2006 | Bavouzet et al. | |
| 2006/0134035 A1 | 6/2006 | Zheng et al. | |
| 2006/0189554 A1 | 8/2006 | Mumper et al. | |
| 2006/0260633 A1 * | 11/2006 | Wyatt et al. | 132/218 |
| 2006/0275232 A1 | 12/2006 | Chevalier | |
| 2007/0020205 A1 | 1/2007 | Blin et al. | |
| 2007/0041920 A1 | 2/2007 | Blin et al. | |
| 2007/0048238 A1 | 3/2007 | Sandewicz et al. | |
| 2007/0140991 A1 | 6/2007 | Maitra et al. | |
| 2007/0274941 A9 | 11/2007 | Blin | |
| 2007/0286824 A1 | 12/2007 | Rabe et al. | |
| 2008/0000491 A1 | 1/2008 | Bodelin | |
| 2008/0014232 A1 | 1/2008 | Arnaud et al. | |
| 2008/0056807 A1 | 3/2008 | Vintimiglia | |

(56) References Cited

U.S. PATENT DOCUMENTS

| | | | |
|---|---|---|---|
| 2008/0107615 A1 | 5/2008 | Keene et al. | |
| 2008/0115798 A1 | 5/2008 | Rainey et al. | |
| 2008/0124350 A1 | 5/2008 | Mumper et al. | |
| 2008/0171009 A1 | 7/2008 | Auguste et al. | |
| 2008/0226575 A1 | 9/2008 | Hanna | |
| 2008/0311063 A1 | 12/2008 | Shah et al. | |
| 2009/0010868 A1 | 1/2009 | Ilekti et al. | |
| 2009/0098170 A1 | 4/2009 | D'Acchioli et al. | |
| 2009/0142282 A1 | 6/2009 | Kendall et al. | |
| 2009/0193692 A1 | 8/2009 | Lipczynski | |
| 2009/0263658 A1 | 10/2009 | Alberius et al. | |
| 2009/0317350 A1 | 12/2009 | Lu et al. | |
| 2010/0003205 A1 | 1/2010 | Elliott et al. | |
| 2010/0003293 A1 | 1/2010 | Elliott et al. | |
| 2010/0028612 A1 | 2/2010 | Gruber et al. | |
| 2010/0068163 A1 | 3/2010 | Lu | |
| 2010/0074928 A1 | 3/2010 | Elliott et al. | |
| 2010/0152135 A1 | 6/2010 | Blin | |
| 2010/0179105 A1 | 7/2010 | Blin et al. | |
| 2010/0285079 A1* | 11/2010 | Imai et al. | 424/401 |
| 2011/0094533 A1* | 4/2011 | Dempsey et al. | 132/216 |
| 2011/0094914 A1 | 4/2011 | Dempsey et al. | |
| 2011/0117040 A1 | 5/2011 | Dempsey et al. | |
| 2011/0117043 A1 | 5/2011 | Dempsey et al. | |
| 2011/0268490 A1 | 11/2011 | Acierto et al. | |
| 2012/0114585 A1 | 5/2012 | Dempsey et al. | |
| 2012/0150029 A1* | 6/2012 | Debuc | 600/425 |
| 2012/0269753 A1 | 10/2012 | Rabe et al. | |
| 2012/0298128 A1 | 11/2012 | Hodgetts et al. | |
| 2012/0315076 A1 | 12/2012 | Bekele et al. | |
| 2013/0012594 A1 | 1/2013 | Hirasawa et al. | |
| 2013/0056016 A1 | 3/2013 | Guay et al. | |
| 2013/0056019 A1 | 3/2013 | Wilson et al. | |
| 2013/0056020 A1 | 3/2013 | Wilson et al. | |

FOREIGN PATENT DOCUMENTS

| | | |
|---|---|---|
| CN | 300856710 | 12/2008 |
| CN | 102360418 A | 2/2012 |
| DE | 3923731 A1 | 1/1991 |
| EM | 000345483.003 | 7/2005 |
| EM | 000386388.0001 | 11/2005 |
| EM | 000386388.0002 | 11/2005 |
| EM | 000386388.0020 | 11/2005 |
| EM | 000386388.0028 | 11/2005 |
| EM | 000386388.0030 | 11/2005 |
| EM | 000386388.0031 | 11/2005 |
| EM | 000386388.0034 | 11/2005 |
| EM | 000500418.001 | 5/2006 |
| EM | 000540869.0021 | 7/2006 |
| EM | 000540869.0024 | 7/2006 |
| EM | 000603808.002 | 11/2006 |
| EM | 000623202.0002 | 12/2006 |
| EM | 000623202.0004 | 12/2006 |
| EM | 000623202.0009 | 12/2006 |
| EM | 000623202.0010 | 12/2006 |
| EM | 000623202.0011 | 12/2006 |
| EM | 000623202.0012 | 12/2006 |
| EM | 000623202.0013 | 12/2006 |
| EM | 000614706.001 | 1/2007 |
| EM | 000654272.0003 | 4/2007 |
| EM | 000654272.0004 | 4/2007 |
| EM | 000654272.0005 | 4/2007 |
| EM | 000688007.0002 | 4/2007 |
| EM | 000688007.0003 | 4/2007 |
| EM | 000871017.0001 | 2/2008 |
| EM | 000871017.0007 | 2/2008 |
| EM | 000871017.0008 | 2/2008 |
| EM | 000871017.0009 | 2/2008 |
| EM | 000871017.0010 | 2/2008 |
| EM | 000871017.0014 | 2/2008 |
| EM | 000871017.0015 | 2/2008 |
| EM | 000871017.0016 | 2/2008 |
| EM | 000871017.0024 | 2/2008 |
| EM | 000871017.0025 | 2/2008 |
| EM | 000871017.0026 | 2/2008 |
| EM | 000871017.0027 | 2/2008 |
| EM | 000871017.0028 | 2/2008 |
| EM | 000871017.0029 | 2/2008 |
| EM | 000871017.0030 | 2/2008 |
| EM | 000871017.0031 | 2/2008 |
| EM | 000871017.0032 | 2/2008 |
| EM | 000871017.0033 | 2/2008 |
| EM | 000871017.0037 | 2/2008 |
| EM | 000871017.0038 | 2/2008 |
| EM | 000871017.0039 | 2/2008 |
| EM | 000871017.0040 | 2/2008 |
| EM | 000871017.0043 | 2/2008 |
| EM | 000871017.0044 | 2/2008 |
| EM | 000871017.0054 | 2/2008 |
| EM | 000871017.0055 | 2/2008 |
| EM | 000871017.0056 | 2/2008 |
| EM | 000871017.0057 | 2/2008 |
| EM | 000871017.0058 | 2/2008 |
| EM | 000871017.0059 | 2/2008 |
| EM | 000871017.0060 | 2/2008 |
| EM | 000871017.0061 | 2/2008 |
| EP | 0024365 B1 | 3/1981 |
| EP | 549494 | 6/1993 |
| EP | 1238603 A3 | 9/2003 |
| FR | 2079785 | 10/1971 |
| FR | 000975286.0001 | 12/1997 |
| FR | 2898469 A1 | 9/2007 |
| FR | 2919477 A1 | 2/2009 |
| GB | 2124081 A | 2/1984 |
| GB | 2293545 A | 4/1996 |
| JP | 03173811 | 7/1991 |
| JP | 2004188189 A | 7/2004 |
| JP | 2004238363 | 8/2004 |
| JP | 2004339212 A | 12/2004 |
| JP | 2006174936 A | 7/2006 |
| JP | 2006282585 | 10/2006 |
| JP | 0D1207926 | 5/2007 |
| JP | 2009114099 | 5/2009 |
| JP | 2009137841 | 6/2009 |
| KR | 300402225.0000 | 12/2005 |
| KR | 300424071.0001 | 2/2006 |
| KR | 300465977.0000 | 10/2007 |
| KR | 300488446.0000 | 4/2008 |
| KR | 300507379.0000 | 9/2008 |
| WO | 96/20698 | 7/1996 |
| WO | 00/47177 | 8/2000 |
| WO | 01/45652 | 6/2001 |
| WO | 2004073662 A1 | 9/2004 |
| WO | 2006/058795 | 6/2006 |
| WO | 2006/078541 | 7/2006 |
| WO | 2008/074870 A2 | 6/2008 |
| WO | 2008089926 A | 7/2008 |
| WO | 2012/011043 A1 | 1/2012 |

OTHER PUBLICATIONS

Avon, Avon, Blueberry Cool/Black Lush Lips and Long Lashes, date published Mar. 2006; www.gnpd.com, 2 pages.

Avon, Avon, Dual Ended Eye-Liner, date published Oct. 2007; www.gnpd.com, 2 pages.

Bobbi Brown Copper Diamond, Everything/Lash Glamour Mascara Duo, date published November 2008; www.gnpd.com, 3 pages.

Bobbi Brown, Honey Glaze Long-Wear Eye Palette, date published Apr. 2009; www.gnpd.com, 3 pages.

Bobbi Brown, Lip and Eye Basics Palette, date published Sep. 2006; www.gnpd.com, 2 pages.

Bobbi Brown, Shimmering Nudes Collection, Shimmering Nudes Palette, date published Oct. 2008; www.gnpd.com, 3 pages.

Caboodles Color Tips, Mascara Extension, date published Dec. 2005; www.gnpd.com, 2 pages.

Helena Rubinstein, Surrealist Mascara & Liner, date published Nov. 2006; www.gnpd.com, 2 pages.

Kao, Aube Couture, Designing Double Mascara, date published Dec. 2008; www.gnpd.com, 3 pages.

Isehan, Kiss Me Mascara Remover, date published Sep. 2008; www-w.gnpd.com, 2 pages.

(56) References Cited

OTHER PUBLICATIONS

Kose, Fasio Mascara Easy Remover, date published Jan. 2009; wwww.gnpd.com, 2 pages.
L'Oréal Double Mascara, Date published May 2006; www.gnpd.com, 2 pages.
MAQuillAGE Shisiedo, Mascara Remover, date published Jun. 2008; wwww.gnpd.com, 2 pages.
Revlon, Limited Edition Dual Lash Mystique Mascara, date published Jun. 2003; www.gnpd.com, 1 page.
Shiseido, The Makeup Eraser Pencil, date published Jun. 2001; wwww.gnpd.com, 2 pages.
Sleek Makeup, Duo Dip It Mascara + Eyeliner, date published Mar. 27, 2009; www.gnpd.com, 3 pages.
SmashBox Limitless Lash Mascara, date published May 2003 wwww.gnpd.com, 2 pages.
SwabPlus Waterproof Mascara Remover Swabs, date published Dec. 2002; wwww.gnpd.com, 2 pages.
Narus Cosmetics, Wink Up Mascara Remover, date published Mar. 1999; wwww.gnpd.com, 1 page.
PCT International Search Report and Written Opinion for PCT/US2010/054090 dated Feb. 16, 2012.
PCT International Search Report and Written Opinion for PCT/US2010/054089 dated Feb. 16, 2012.
R.E. Lobnig et al., "Development of a new experimental method to determine critical pigment-volume-concentrations using impedance spectroscopy", Progress in Organic Coatings 55 (2006) 363-374.
S.H.M. Gibson et al., "Determination of the critical pigment volume contrations of pigmented film coating formulations using gloss measurement", International Journal of Pharmaceutics 45, (1988) 245-248.
F. Zulli et al., "Preparation and properties of small nano particles for skin and hair care", SOFW Journal 123, Jahrgang 13/97 p. 880-885.
PCT International Search Report and Written Opinion for PCT/US2013/038339 dated Sep. 12, 2013.
R. Pigeon and P. Allard, Chimie Macromo-culaire Applique, 40141 (1974), pp. 139-158 (No. 600).
PCT International Search Report and Written Opinion for PCT/US2012/038231 dated Aug. 21, 2012.
Avon, Avon, Shimmer Shadow and Liner, date published Jun. 2007; www.gnpd.com, 2 pages.
Avon, MistakeProof Mascara, date published Oct. 2008; www.gnpd.com , 4pages.
Bare Escentuals, bareMinerals Tutorials, Lesson 1: Get Cheeky, date published Feb. 2008; www.gnpd.com, 1 page.
Bare Escentuals, bareMinerals, Get Started: Eyes, Cheeks, Lips Set, date published Mar. 2008; www.gnpd.com, 1 page.
Bobbi Brown, Bobbi Brown Christmas 2008, Night Sky Long-Wear Eye Palette, date published Dec. 2008; www.gnpd.com, 3 pages.
Cosmetobelleza Natural IM , Double Effect Mascara, date published: Jul. 2009; www.gnpd.com, 2 pages.
Creative Brands, Australis, Eyeshadow, date published Aug. 2007; www.gnpd.com, 2 pages.
Del Laboratories, Sally Hansen Healing Beauty, Thicken-Up Plumper + Mascara, date published Oct. 2003; www.gnpd.com, 2 pages.
Gurwitch Products, Laura Mercier, Limited-Edition Eye Book, date published Dec. 2008; www.gnpd.com, 2 pages.
Gurwitch Products, Laura Mercier, Beauty Library Set, date published Dec. 2006; www.gnpd.com, 3 pages.
Invima, Isadore Wonder Full Mascara, date published Sep. 2006; www.gnpd.com, 2 pages.
Kose, Fasio Easy Mascara Remover, date published Jun. 2009; wwww.gnpd.com, 3 pages.
Lorac Cosmetics, Lorac, Fairytale Life Makeup Collection, date published Dec. 2007; www.gnpd.com; 4 pages.
Napoleon Perdis Cosmetics, NP Set Eyeliner, date published Mar. 2009; www.gnpd.com, 4 pages.
Napoleon Perdis Cosmetics, NP Set, Eye Palette, date published Feb. 2009 www.gnpd.com, 3 pages.
Prestige Cosmetics, Glitter Lash Mascara, date published Dec. 2008, www.gnpd.com, 2 pages.
Rimmel , Coty, Volume Extend Waterproof Mascara, date published Sep. 2006; www.gnpd.com, 2 pages.
Rimmel, Double Play Multi Look Mascara, date published Apr. 2007; Mar. 2007; www.gnpd.com, 2 pages.
Rossman, Rival de Loop Young, Double Brush Mascara, date published: Oct. 2009; www.gnpd.com, 2 pages.
Swab Plus Eye Makeup Remover Swabs , date published Nov. 2007; wwww.gnpd.com, 2 pages.
Tarte Cosmetics, Tarte Fall 2008, Eye Couture Day-to-Night Eye Palette, date published Aug. 2008; www.gnpd.com, 2 pages.
The Art of Makeup, VIP Complete Cosmetic Kit, date published Feb. 2008; www.gnpd.com 4 pages.
Xtreme Color, Mary-Kate and Ashley, Eye Drama Creme Eye Color Plus Rich Mascara, date published Jul. 2004; wwww.gnpd.com, 2 pages.
Yves Saint Laurent; Yves Saint Laurent Parfums; Duo Expert Sourcils, date published Nov. 2004; www.gnpd.com, 1 page.
PCT International Search Report and Written Opinion for PCT/US2013/041135 dated Nov. 8, 2013.
PCT International Search Report and Written Opinion for PCT/US2010/054085 dated Feb. 23, 2012.
PCT International Search Report and Written Opinion for PCT/IB2008/050102 dated Jun. 9, 2008.
PCT International Search Report and Written Opinion for PCT/US2010/054079 dated Feb. 23, 2012.
PCT International Search Report and Written Opinion for PCT/US2011/033429 dated Jun. 1, 2011.
PCT International Search Report and Written Opinion for PCT/US2011/057104 dated Feb. 21, 2012.
J. Jachowicz et al., "The effect of the amphiprotic nature of human hair keratin on the adsorption of high charge density cationic polyelectrolytes", Colloid and Polymer Science 263: 847-858 (1985).
Masaki Okazaki et al., "Introduction of cationic groups onto carbon black surface and their dispersibility in water", J. Dispersion Science and Technology 21(5), 511-524 (2000).

* cited by examiner

METHOD FOR QUANTITATIVELY DETERMINING EYELASH CLUMPING

FIELD OF THE INVENTION

The present application is directed, generally, to a method for quantifying clumping in fibrous materials. Specifically, methods for quantifying clumping in keratinous materials such as eyelashes when a composition such as mascara is applied thereto are disclosed herein.

BACKGROUND OF THE INVENTION

Mascara compositions have been used for many years to increase the thickness, length, and overall aesthetic appearance of human eyelashes and/or eyebrows. Consumers often expect particular properties from their mascara products such as adhesion to the lashes, lengthening/curling of the lashes, lack of smudging or flaking, thick lashes, and good separation of clumps of lashes. Particularly, the desire may be for long, luscious, full, soft, and separated lashes. Mascaras generally distribute a smooth and relatively thin (coating thickness) film over the eyelashes producing a satisfactory array of reasonably separated lashes that are darker and thicker than bare lashes, making the eyes more noticeably beautiful. In particular, at least some consumers desire a mascara to increase the volume of the eyelashes to make the eyelashes more noticeable. There are a variety of conventional mascaras available that claim to provide improved eyelash volume. Such mascaras are sometimes referred to as volumizing mascaras or volumizers. But in order to provide the increased volume, the volumizers may be formulated as a relatively thick (i.e., viscous) composition. In some instances, the applicator to apply the thicker volumizing mascara needs to be configured to apply thick compositions (e.g., larger core, increase spacing between bristles), which may not be as good for eyelash separation as applicators with a smaller core or closer bristle spacing.

Eyelash separation is also considered important for improving the appearance and noticability of eyelashes. Some mascara products are known to cause eyelash "clumping." Clumping occurs when two or more eyelashes or eyelash portions stick to one another. Typically, the deposition of mascara has a coating that is 5-15 microns thick. But at least some volumizing mascaras tend to clump too many lashes together in a thick, less separated look which gives the perception of fewer lashes. While it is well understood that some lash clumping will naturally occur since lashes are arranged in both rows and columns above and below one's eye, complete separation of eyelashes is the "ideal" standard to be attained. A mascara product that is deemed by a user to separate well leaves fewer clumps of lashes than mascara that is deemed not to separate lashes well.

Producers of mascara products recognize that consumers desire a mascara product that provides improved volume and separation, and strive to design such a product. But there is currently no readily acceptable way to quantify eyelash clumping such that different mascara products (e.g., formulas, applicators, and the combinations of these) can be compared to one another in a standardized way. Rather, most manufacturers of mascara products rely on consumer opinions (e.g., test panelists) and/or other qualitative methods to determine whether a particular product provides sufficient eyelash separation. Qualitative methods may be sufficient for determining whether consumers perceive a particular product as providing desirable separation, but may not be suitable for product modeling/simulation and/or for supporting advertising claims directed to improved separation, especially when comparing a competitive product.

Accordingly, it would be desirable to provide a method for quantitatively determining the amount of eyelash clumping present when using a mascara product.

SUMMARY OF THE INVENTION

In order to provide a solution to the aforementioned problem, disclosed herein are methods for quantitatively determining eyelash clumping. In some examples, the method comprises: providing an eyelash substrate comprising an array of eyelashes, each eyelash having a length defined by a base and an opposing tip; applying an amount of mascara to the eyelashes; capturing an image of the eyelashes with the mascara applied thereto; analyzing a first portion of the image to obtain first individual thickness measures for each eyelash disposed in the first portion; analyzing a second portion of the image to obtain second individual thickness measures for each eyelash disposed in the second portion; obtaining first average thickness measures from the first individual thickness measures and second average thickness measures from the second individual thickness measures; applying a weighting function to the first and second average thickness measures to generate first and second weighted thickness values; and obtaining a Weighted Average Thickness value from the first and second average thickness measures to provide a quantitative determination of eyelash clumping.

DETAILED DESCRIPTION OF THE INVENTION

All percentages are by weight of the personal-care composition, unless otherwise specified. All ratios are weight ratios, unless specifically stated otherwise. All numeric ranges are inclusive of narrower ranges and the upper and lower range limits Delineated upper and lower range limits are interchangeable to create further ranges not explicitly delineated. The number of significant digits conveys neither limitation on the indicated amounts nor on the accuracy of the measurements. All measurements are understood to be made at about 25° C. and at ambient conditions, where "ambient conditions" means conditions under about one atmosphere of pressure and at about 50% relative humidity.

While the disclosure below may describe the present method in terms of eyelash and clumping resulting from the application of mascara, it is to be appreciated that one of ordinary skill in the art could practice the present method to great advantage to quantitatively determine the clumping of any fibrous material.

DEFINITIONS

"Clump" and variations thereof mean two or more eyelashes or eyelash portions that are joined to one another.

"Joined" means configurations whereby an element is directly secured to another element by affixing the element directly to the other element. For example, two or more eyelashes may be joined to one another with mascara to form a clump.

"Keratinous tissue," means keratin-containing tissue layers disposed as the outermost protective covering of mammals which includes, but is not limited to, hair.

"Mascara" and "mascara composition" mean a liquid cosmetic composition that is applied to eyelashes to provide an aesthetic benefit or change in appearance such as, for example, the appearance of a color change, a volume change, and/or a length change. Mascara may also be applied to eyelids, and/or eyebrows. The present mascara compositions are formulated for topical application to mammalian keratinous tissue for use in cosmetic products. The methods of using mascara compositions are also included within the meaning of mascara composition.

Weighted Average Thickness (W.A.T.) Test

Mascaras tend to coat lashes differently depending on the combination of formula and brush (e.g., the size of the brush and/or configuration of the bristles). Some mascaras are dumped at the base of the lashes upon first contact of the brush with the lash and only a small amount of mascara is moved along the shaft of the lashes to the tips. This may result in an undesirable difference between the thickness increase at the base of the lash versus the tip of the lash. That is, the volume benefit that some users desire may not appear to be evenly distributed along the lash. In some instances, the mascara brush may be more effective at coating the eyelashes disposed near the center portion of the eyelid versus the eyelashes disposed near the edge(s). This may depend on the ability of the brush to hold the mascara along the entire length of its core. Mascara brushes that load in the center of the core but not at the tip will give inconsistent coating from one end of the eyelash array to the other. Thus, it is important to measure mascara deposition in terms of lash thickness transformation across all lashes in order to map an accurate picture of their performance efficacy.

A suitable mascara product should provide good lash separation without undesirable clumping, which is commonly perceived by consumers as the main failure mechanism of a mascara product. Mascara related clumping generally occurs when the mascara product causes individual eyelashes to stick together and form clumps. Clumping at the base of eyelash may be acceptable to some consumers, but clumping at other portions of the eyelash, especially the tips, is generally unacceptable. Separation, as the name implies, is the perception by a consumer that the individual eyelashes are discernible such that they exhibit the length, curl, and/or volume beauty benefit desired from the mascara product. Thus, a mascara product may cause some clumping at the base of the eyelash, but if there is good separation acceptable beauty benefits may still be obtained.

Figure 1A:
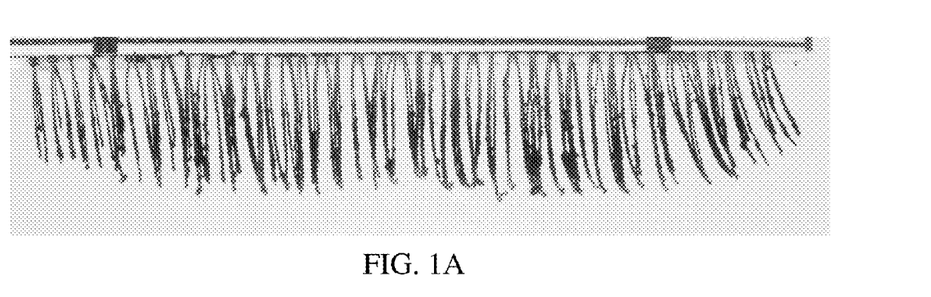
FIG. 1A is a photograph of an eyelash substrate with mascara applied thereto.
Figure 1B:
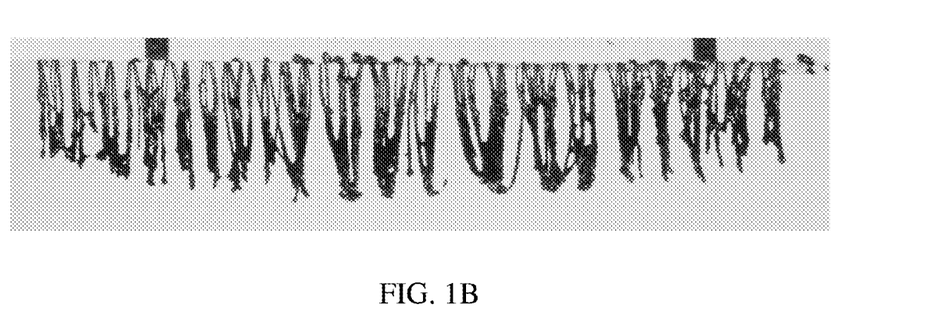
FIG. 1B photograph of an eyelash substrate with mascara applied thereto.

FIGS. 1A and 1B illustrate the effect of clumping related to the use of mascara. A mascara composition was applied to artificial eyelashes in FIG. 1A with a twisted-wire brush. The same mascara composition was applied to the artificial eyelashes shown in FIG. 1B with a molded plastic brush. The eyelashes in FIG. 1A exhibit improved separation and less clumping compared to the eyelashes illustrated in FIG. 1B.

The W.A.T. Test described herein provides a method to reproduce the effect of applying mascara compositions to typical human eyelashes and quantify certain qualitative mascara effects on lashes. In particular, the W.A.T. test may be used to quantify the clumping characteristics associated with applying mascara to typical human eyelashes. The W.A.T. value may be determined after applying mascara to a suitable eyelash substrate with one or more strokes (e.g., 1, 2, 3, 4, 5, 6, 7, 8, 9 or 10). It is believed, without being limited by theory, that five strokes may be of particular interest because it corresponds to the "beauty end state." That is, it is believed that the typical user of mascara moves the applicator along the length of the eyelashes five times when applying mascara. However, W.A.T. values at 1 stroke and 3 strokes or other numbers of strokes may also be helpful when evaluating the clumping characteristics of a mascara formulation, especially regarding "dump and fix" type mascara use. Dump and fix generally means applying a dose of mascara to the eyelash on the first stroke ("dump") and using subsequent strokes to obtain a desired look ("fix"), for example, by distributing the mascara homogenously along the length of the eyelash. Dumping the mascara typically results in high clumping, and the subsequent fixing is important to understand how well the mascara and brush combination reduce undesirable clumping. In other words, a dump and fix clumping profile can be developed for a mascara product, and thus enable product differentiation based on clumping. In particular, the change in W.A.T. value between the first and third stroke, the first and fifth strokes, or even the third and fifth stroke may provide an important indication of the clumping characteristics of a mascara product.

The W.A.T. test utilizes an eyelash substrate to quantitatively determine clumping. The eyelash substrate should include a plurality of eyelashes that represent the thickness and length of a typical human eyelash (e.g., Ardell 109 brand Fashion Lashes, which are made of natural human hair). While artificial eyelash substrates are exemplified herein, it is to be appreciated that the present method also contemplates determining the W.A.T. value of mascara-coated eyelashes in vivo. The eyelash substrate maybe secured to a rigid backing material that may be suitably repositioned as needed during testing. Once secured to the rigid backing, mascara may be deposited on the eyelashes of the eyelash substrate with a suitable applicator. An image of the eyelashes before and after depositing mascara thereon may be obtained. The image of the bare eyelashes (i.e., before mascara has been applied) may be used as a template to compare to the mascara-containing lashes for dimensional analysis. To obtain an image, it may be desirable to use a suitable camera to capture an image of the eyelashes. Non-limiting examples of suitable cameras include digital single-lens reflex ("DSLR") cameras with a resolution of 7 megapixels or greater. A particularly suitable example of a camera 1640 is a Nikon D90 SLR brand camera, equipped with a 105 mm Macro Lens. Once the image is captured, the image may be transferred to a computer for image analysis using, for example, suitable image analysis software such as ImageJ, which is an open-source, java-based image analysis program. The image analysis software may be used to modify the image to a more usable form and obtain relevant data from the image. The data thus obtained is outputted for further analysis by programmable data analysis software such as MICROSOFT EXCEL. Using the data analysis software, the W.A.T. value and other characteristics of the eyelash array may be determined.

The following description and the accompanying figures will be used to exemplify the method used to determine the W.A.T. value. It is to be appreciated that the method herein is not limited to such examples, but contemplates other embodiments, which may include modifications that are within the skill of the ordinary artisan.

Figure 2:
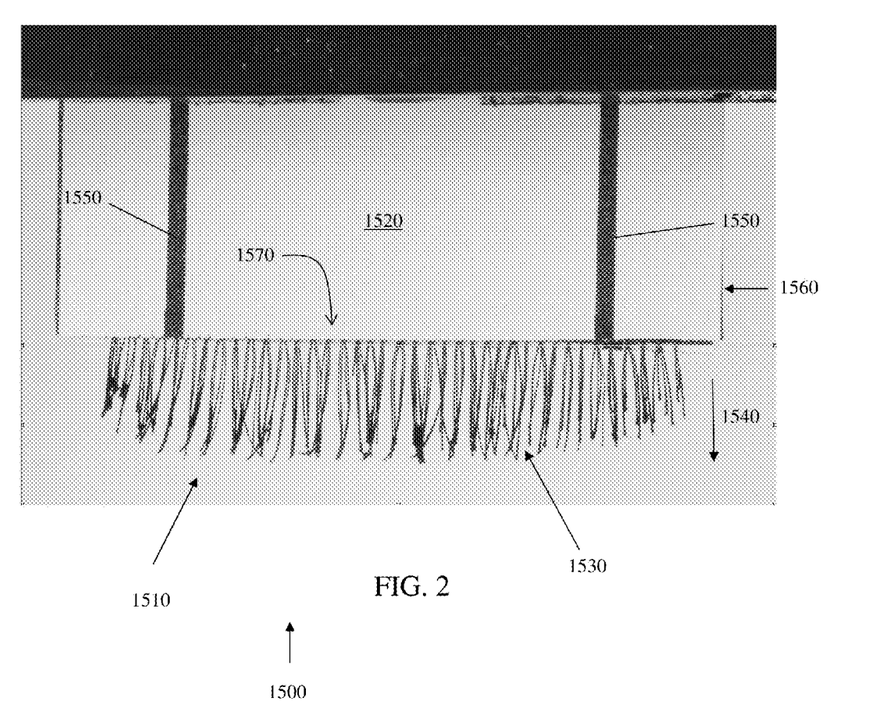
FIG. 2 is a photograph of an eyelash substrate joined to a repositioning template.

FIG. 2 shows a captured image 1500 of an eyelash substrate 1510, which includes an array of individual eyelashes, affixed to repositioning template 1520. Referring to FIG. 2, a clean, undamaged eyelash substrate 1510 (i.e., no bent or misshapen eyelashes) is attached to a repositioning template 1520 made from a white paper or card material cut to 4 cm×4 cm. The repositioning template 1520 is used to help ensure that the base 1570 of the eyelash substrate 1510 is substantially straight, as opposed to the arc it may naturally be bent in. Thus, the eyelashes in the eyelash substrate 1510 should all point in substantially the same direction for analysis, as indicated by the arrow 1540 in FIG. 2. A black tram line 1550 is provided (e.g., with a suitable black marker or pen) 1 cm from each outer edge 1560 of the repositioning template 1520, as shown in FIG. 2. The tram lines 1550 are positioned just inside the lash array space and act as anchor points for the ghosting software, which is described in more detail below.

With the eyelash substrate 1510 attached to the repositioning template 1520, mascara is applied to the eyelashes in a fixed dosing pattern: 1 stroke, 3 strokes, and 5 strokes (or any number of strokes desired, e.g., 6, 7, 8, 9, or 10) to show the loading effect on the lashes and mascara deposition efficiency (i.e. building physical volume per lash without creating clumps). Each stroke typically requires two brush/lash interactions or "swipes" to contact all of the eyelashes of the eyelash substrate 1510 (i.e., one swipe from the left side and one from the right side). A stroke should start by contacting the mascara applicator with the base 1570 of the eyelashes and moving the brush along the length of the eyelashes to the tips 1530. The first, third and fifth stroke data are believed to be particularly important for determining the degree of user satisfaction, as this corresponds to the number of strokes commonly used by a consumer when applying mascara. In a particular suitable example, the mascara is applied directly to the eyelashes by person, as opposed to by a machine or by a person operating a machine.

To obtain the mascara, remove the mascara applicator carefully from the mascara package by pulling the brush and wand directly outwards (i.e., do not "pump" the pack) and discard any globs of mascara present on the tip of the brush (e.g., using a tissue). Hold the edge of the template 1520 such that the eyelashes point away from you at a downward angle of 45 degrees. Hold the brush perpendicularly to the lashes proximate the base 1570 of the eyelash substrate 1510. Contact the mascara brush with the eyelashes at the base 1570 and move the brush along the length of the eyelashes 1530 in a continuous, uniform motion towards the tip 1530 of the eyelashes. It should take approximately 1-2 seconds to move the brush along the length of the eyelashes from the base 1570 to the tips 1530. During application, the brush may be rotated one quarter of a turn as it reaches the tips 1530 of the eyelashes. Perform the application process for both the left and right sides of the eyelash substrate 1510. For each subsequent stroke after the first, do not add additional product onto the applicator brush. In addition, during application, the brush should not be rolled or tilted along the lashes in a way that increases the application pressure or alters the application speed.

Figure 3A:
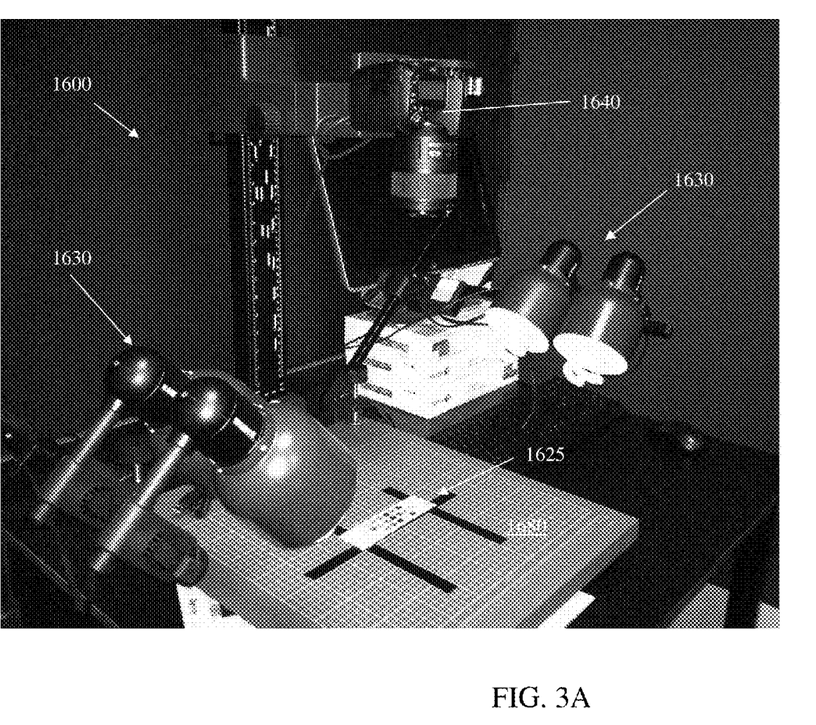
FIG. 3A-3C are a photographs of an imaging rig.

FIG. 3A illustrates an exemplary imaging rig 1600 suitable for use in capturing an image of an eyelash substrate for analysis. The imaging rig 1600 includes a rigid horizontal surface 1680 suitable for supporting a repositioning template 1620 in combination with an eyelash substrate 1610. The imaging rig 1600 also includes one or more lights 1630 and a camera 1640 positioned to capture an image of a target image area 1625. The target image area 1625 should be sized to completely contain the repositioning template 1620 and eyelash substrate 1610, and should be positioned within the controlled lighting/camera setup to enable the camera 1640 to capture an image of the entire target image area 1625.

Figure 3B:
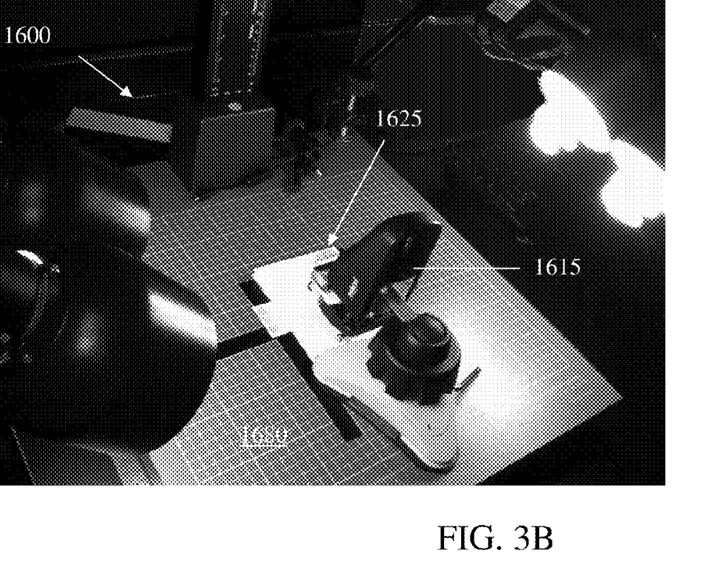
Figure 3C:
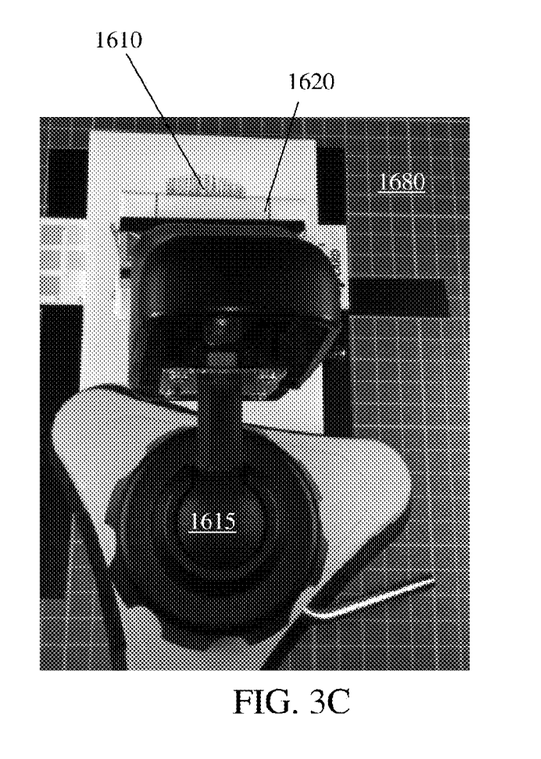

As illustrated in FIG. 3B, the repositioning template 1620, which includes the eyelash substrate 1610, is secured to the horizontal surface 1680 of the imaging rig 1600 with a vice 1615. The repositioning template 1620 and the eyelash substrate 1610 are both positioned in the target image area 1625. FIG. 3C is a close-up view of the repositioning template 1620 secured to the horizontal surface 1680 of the imaging rig 1600. To help ensure that the camera 1640 captures an image with sufficient resolution for subsequent image analysis, the camera 1640 may be positioned such that the lens of the camera 1640 is between 25 and 75 cm above the repositioning template 1620 and eyelash substrate 1610 (e.g., 35-65 cm, 40-60 cm, or about 50 cm). In addition, it may be desirable to position the lights 1630 on either side of the repositioning template 1620 to provide sufficient illumination. The exposure time, aperture and/or ISO of the camera 1640 should be set to capture an image that is suitable for analysis by the image analysis software (e.g., exposure time/shutter speed set to 0.25 second, aperture set to 32 and ISO set at 200). Once the camera 1640 is configured to capture a suitable image, which may include manual focusing, a picture of the image target area 1625 is taken.

Figure 4A:
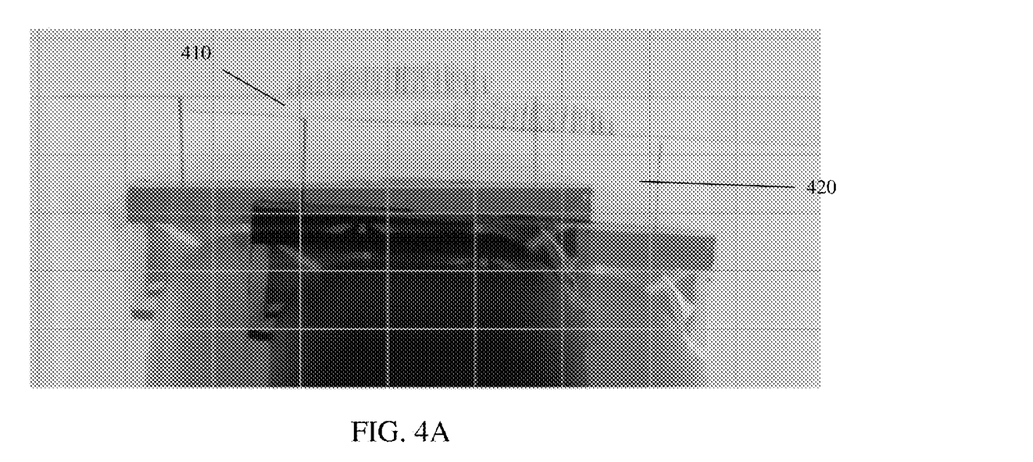
FIG. 4A is a screen shot of unaligned images.
Figure 4B:
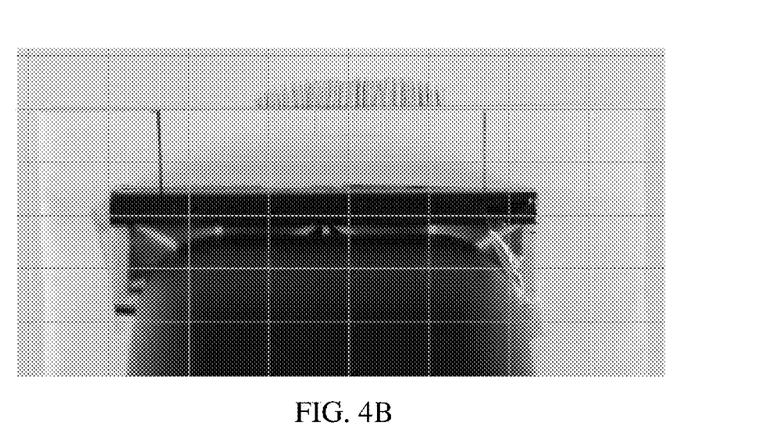
FIG. 4B is a screen shot of aligned images.

In some instances, it may be desirable to capture an image of the bare eyelash substrate (i.e., with no mascara) either alone or in combination with the repositioning template to use as a ghost image. In such instances, the camera 1640 should include "ghosting technology," which is an imaging software program that typically comes with a DSLR-type camera. The ghosting function enables a user to capture an image and set it as a reference guide (i.e., the "ghost image"). This is important because the ghost image can be opened as a background to a "live" image (i.e., the captured image that is currently being viewed/analyzed), which enables a user to reposition the live image relative to the ghost image. For example, when a live image is captured and displayed by a computer, a user can use the ghosting function to superimpose the live image over the ghost image and align the live image with the ghost image. FIG. 4A illustrates a ghost image 410 and a live image 420 that are superimposed but not aligned. FIG. 4B illustrates an aligned ghost image and live image.

Figure 5A:
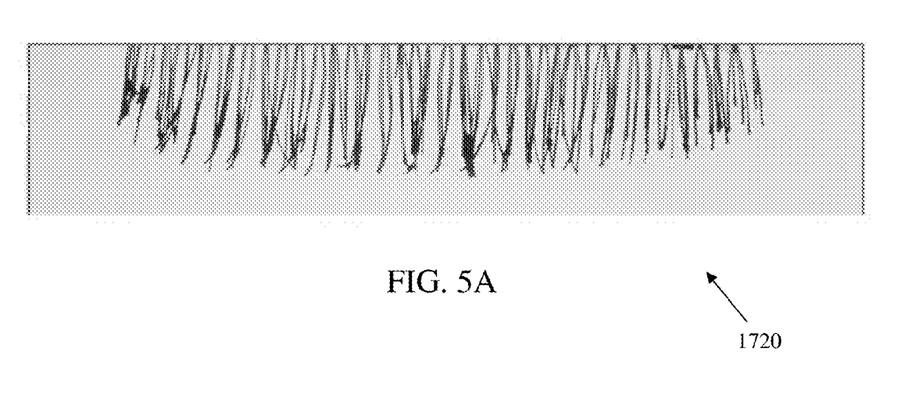
FIG. 5A is a captured image of an eyelash substrate joined to a repositioning template.

Using image analysis software, the captured image 1500 from FIG. 2 may be cropped to provide a cropped image 1720, as illustrated in FIG. 5A. In FIG. 5A, the illustrated image is cropped to remove the repositioning template from the image, but it is to be appreciated that the image may be cropped to any dimension, as desired. In particular, the live image may be placed over the ghost image and cropped to match the dimensions of the ghost image. The resolution of the image (i.e., the number of pixels per centimeter) may vary depending on the resolution of the camera and/or image analysis software. To standardize measurements for the method disclosed herein, a spatial calibration measurement should be conducted and the images should be calibrated so that 1 pixel=10.4 microns. As used hereafter, 1 pixel is equivalent to 10.4 microns. Many digital cameras have the capability to calibrate directly at the time of image capture. Spatial calibration may also be performed after image capture using certain image analysis software.

Figure 5B:
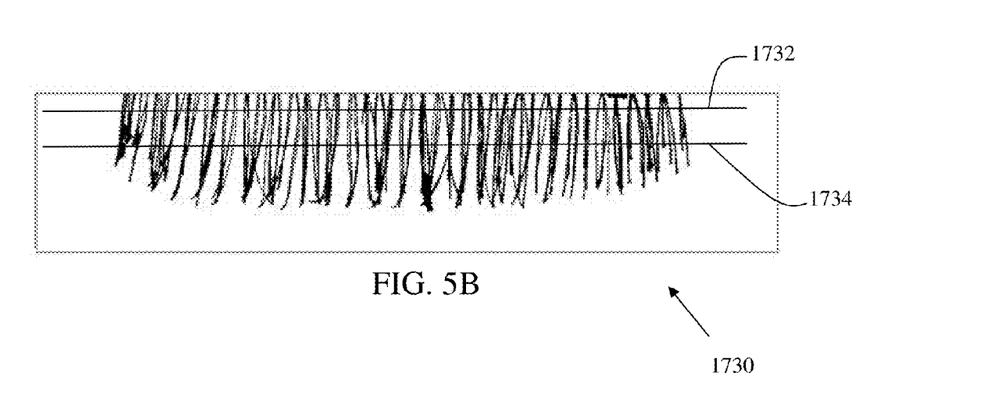
FIG. 5B shows the captured image of 5A after being cropped and converted to a binary image.
Figure 5C:
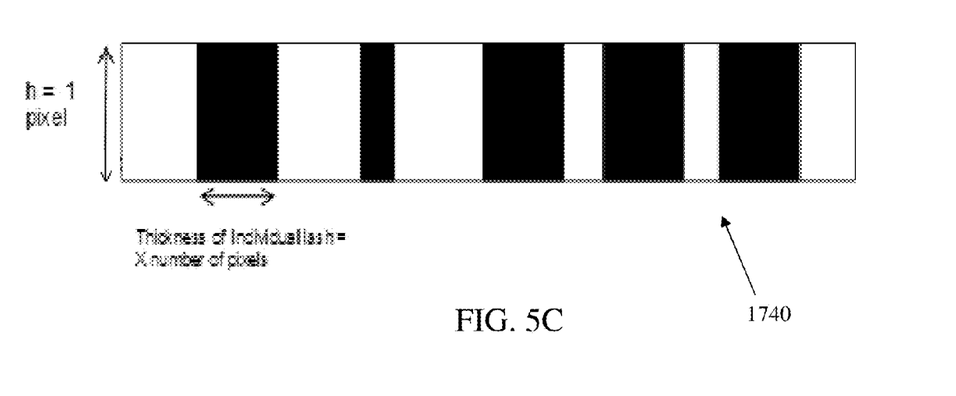
FIG. 5C shows a slice of the captured image of 5B after being convered into a barcode image by image analysis software.

Again using the image analysis software, the cropped image 1720 is converted to a binary image 1730 (i.e., black and white), as illustrated in FIG. 5B. The binary image 1730 is then "sliced" into a barcode image 1740 by the image analysis software, as illustrated in FIG. 5C. In other words, the image analysis software collects data along imaginary lines drawn across the array of eyelashes, such as lines 1732 and 1734. Any number of imaginary lines 1732 and 1734 may be provided across all and/or a portion of the array at predetermined intervals. For example, the image analysis software may be set to draw the imaginary lines across the total lash array at a set spacing along the entire length of the eyelashes (i.e., starting at the base of the lashes and finishing at the tips). The barcode image may have a height (i.e., line thickness) of between 1 and 5 pixels (e.g., 1, 2, 3, 4, or 5). A height of 1 pixel is particularly suitable. It is important that the height not exceed 5 pixels or the sensitivity of the analysis may be too dulled to suitably pick out differences in thickness as the scan progresses along the length of the eyelash. In addition, using a height of greater than 5 pixels may result in fewer data points, which decreases the accuracy of the averages across the total scan and limits how accurately the clumping effect of different mascara products can be distinguished from one another. The slices of data collected by the image analysis software may be spaced apart along the length of the eyelash. For example, the slices of data may be separated by from 1 to 10 pixels (e.g., 2, 3, 4, 5, 6, 7, 8 or 9) at a resolution. Collecting the slices of data at 10 pixel intervals is particularly suitable. It has been found that separating the data slices by more than 10 pixels can dull the sensitivity of the analysis because key areas of information may be missed. But surprisingly, separating the data slices by less than 10 pixels does not seem to noticeably improve sensitivity. In some instances, the image analysis software may be configured to analyze non-linear portions of all or some of the eyelash array. For example, the eyelash array be broken into a first portion that includes the middle of the eyelash substrate (when view from end to end), a second portion that includes the eyelashes disposed at one end of the eyelash substrate and a third portion that includes eyelashes disposed at the opposing end of the eyelash substrate. In this way, clumping that occurs in the middle of the eyelashes could be compared to clumping at the edges.

Each slice of data (i.e., barcode image) is analyzed by the image analysis software for the number of black regions and the thickness of each black region in pixels, which is outputted to the data analysis program for further processing. The programmable data analysis software manipulates the output data to generate an average thickness measurement for each barcode image. Unaltered lashes (e.g., lashes that have the same thickness as when untreated) are not included in the calculation of the average thickness measurement. Unaltered lashes are defined as those lashes with a thickness of less than 23.75 pixels. Based on measurements across a broad sample of artificial eyelashes made from 100% human hair, it was found that the thickness of these lashes are generally less than 23.75 pixels. Thus, the weighting function is only applied to lashes of a thickness greater than 23.75. Lashes above 23.75 pixels may be progressively weighted by the following weighting function:

$$Y=0.0675x^2-23.75x+225.$$

Where:
Y=weighted thickness for the barcode image and
x=average thickness of the black regions of the barcode image The W.A.T. value for the eyelash substrate is calculated by averaging the individual weighted thickness values. This procedure may be repeated two more times and the average of the three W.A.T. values may be calculated to obtain an Average W.A.T. value. A larger W.A.T. value corresponds to a higher clumping level, and consequently a more negative consumer perception or rating. Thus, larger clumps are given a higher weighting than smaller clumps so 1 large clump will give a higher W.A.T. value than two smaller ones. This is important because consumers perceive a single large clump more negatively than several small clumps.

EXAMPLE

Several conventional multi-day/long-wear mascaras and a lash stain were tested to compare the clumping effect of the various mascaras. Table 1 shows the name and code of the mascara tested and illustrates the average W.A.T. value at 1 stroke, 3 strokes and 5 strokes. The brush used to apply each of the comparative mascaras is the brush that is sold with the commercially available product. A general description of the brush is provided in Table 1. Prototype 036, which is a semi-permanent mascara composition described in copending U.S. Provisional Ser. No. 61/487,149, was applied with a rubber brush and a twisted wire brush to demonstrate the reduced clumping benefit. The rubber brush is a Shape 4 molded plastic brush available from GEKA, GmbH. The twisted wire brush is a 2000 Calorie brand twisted wire brush available from Alcan Packaging Beauty Services, France. The mascaras tested were Clinique® Lash Power® brand mascara, Clinique® High Impact Curling™ brand mascara, Tarte® 4 day brand lash stain, Max Factor® False Lash Effect 24® brand mascara, Maybelline® Define-a-Lash® brand waterproof mascara, Maybelline® Volume' Express® Falsies® brand waterproof mascara, Lorac® 3 day brand mascara, Santoprene® brand mascara, Hard Candy® brand mascara and L'Oreal® Beauty Tubes™. The clumping level was determined according to the W.A.T. Test described above.

TABLE 1

| Product | Brush type | Code | | Average W.A.T value |
|---|---|---|---|---|
| Clinique Lash Power | twisted wire | CLP | 1 Stroke | 51.6 |
| | | | 3 stroke | 52.2 |
| | | | 5 Stroke | 56.8 |
| Clinique High Impact Curl | twisted wire | CHI | 1 Stroke | 39.8 |
| | | | 3 stroke | 43.1 |
| | | | 5 Stroke | 45.0 |
| Tarte 4 day | twisted wire | TA | 1 Stroke | 20.8 |
| | | | 3 stroke | 31.1 |
| | | | 5 Stroke | 31.3 |
| prototype 036 | twisted wire | GTWB | 1 Stroke | 30.7 |
| | | | 3 stroke | 22.9 |
| | | | 5 Stroke | 24.7 |
| prototype 036 | rubber | GS | 1 Stroke | 67.1 |
| | | | 3 stroke | 69.7 |
| | | | 5 Stroke | 69.3 |

TABLE 1-continued

| Product | Brush type | Code | | Average W.A.T value |
|---|---|---|---|---|
| False Lash Effect 24 | rubber | FLE 24 | 1 Stroke | 33.1 |
| | | | 3 stroke | 35.8 |
| | | | 5 Stroke | 38.0 |
| Maybelline Define A Lash Water proof | rubber | MDAL | 1 Stroke | 22.7 |
| | | | 3 stroke | 25.2 |
| | | | 5 Stroke | 36.4 |
| Maybelline Define A Lash | Rubber | MDAL R | 1 Stroke | 25.5 |
| | | | 3 stroke | 28.1 |
| | | | 5 Stroke | 27.8 |
| Maybelline Falsies Water proof | twisted wire | MFWP | 1 Stroke | 32.9 |
| | | | 3 stroke | 46.7 |
| | | | 5 Stroke | 55.1 |
| Lorac 3 day | twisted wire | L3D | 1 Stroke | 19.2 |
| | | | 3 stroke | 26.8 |
| | | | 5 Stroke | 31.5 |
| Hard Candy | twisted wire | HC | 1 Stroke | 20.7 |
| | | | 3 stroke | 28.6 |
| | | | 5 Stroke | 36.0 |
| Beauty tubes (2 Step) | twisted wire | BT | 1 Stroke | 39.1 |
| | | | 3 stroke | 41.7 |
| | | | 5 Stroke | 46.0 |
| Beauty tubes top coat only | twisted wire | BT1 | 1 Stroke | 33.1 |
| | | | 3 stroke | 34.9 |
| | | | 5 Stroke | 41.5 |

Figure 6:
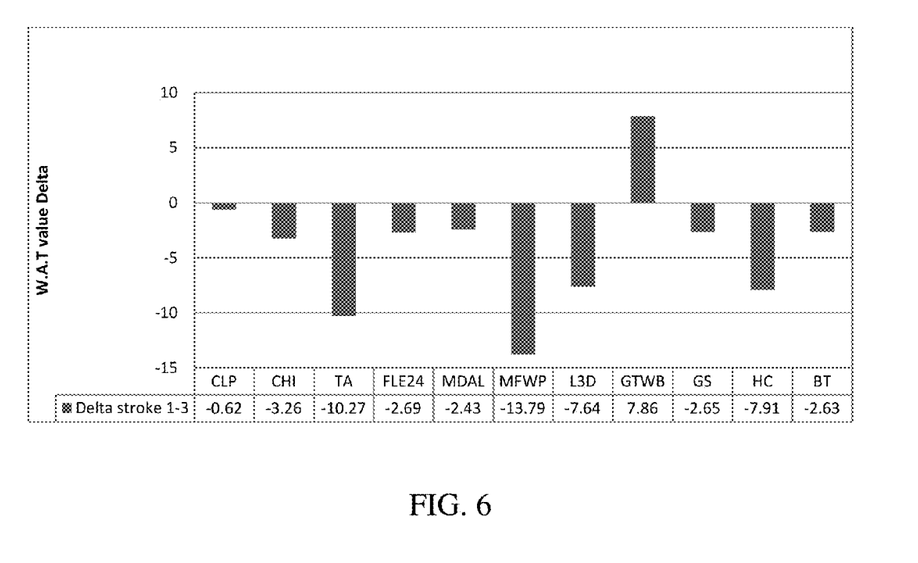
FIG. 6 illustrates the change in W.A.T. value from the first to the third stroke for a variety of mascaras.

As seen in Table 1, the W.A.T. test can be used to quantitatively determine the clumping effect of a mascara product. Prototype 036, when used in combination with a twisted wire brush provides superior anti clumping benefit at the beauty end state (i.e., fifth stroke). In addition, as illustrated in FIG. 6, the prototype 036 in combination with the twisted wire brush is the only sample tested to exhibit a positive value when going from the first stroke to the third stroke (sometimes referred to as a "dump and fix" profile). That is, the first stroke W.A.T. value is greater than the third stroke W.A.T. value, which indicates a reduction in clumping from the first stroke to the third stroke. The W.A.T. values illustrated in Table 1 correspond to qualitative determinations of clumping.

Consumer Test

A study was conducted to assess the visual wear advantages of a mascara composition when applied with a suitable twisted-wire brush versus applying the same product with a molded plastic brush. The twisted-wire brush used in the consumer test is commercially available in Cover Girl® Professional Super Thick Lash brand mascara product. Each wire in the twisted-wire core of the applicator has a wire diameter of 0.70 mm; a brush head length of 25.4±1.52 mm; 600±30 hollow bristles; and the twisted wire core has 18±1 turns. The molded plastic brush was a Shape IV molded plastic brush available from GEKA GmbH, Bechhofen, Germany. The plastic molded brush has a core diameter of 2.28±1 mm; a brush length of 25.6±0 3 mm; a maximum brush diameter of 7.75±0.25 mm; and 228 bristles.

Prior to the application of mascara, images were taken of clean, bare lashes (baseline) using a fixed rig to minimize movement during image capture. For the image capture, panelists were instructed to look up so that the full arc of top lashes could be seen against the brow bone. Panelists were then instructed to apply the mascara until they got to their desired end look. Images were taken immediately after application of the mascara, and at 24 hours (beginning of day 2). The images were captured on a Fujifilm FinePix S1Pro™ brand camera using an external flash with a focal length of 105 mm. The brush type (Shape IV and Twisted Wire Brush) were tested simultaneously on each panelist (one brush type per eye). The order of application and left or right eye for each brush were randomized. The qualitative results obtained from consumer test (i.e., which mascara product appeared to cause the most clumping) support the quantitative determination of clumping using the W.A.T. Test.

Figure 7A:
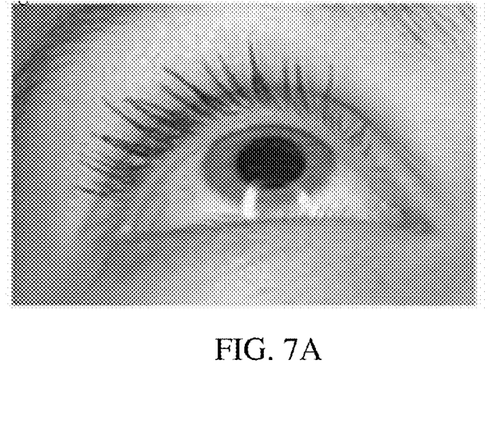
FIGS. 7A-7B are photographs that illustrate the eyelashes of a test subject after application of mascara with a molded plastic brush.
Figure 7B:
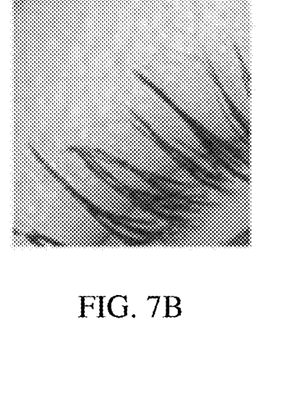
Figure 8A:
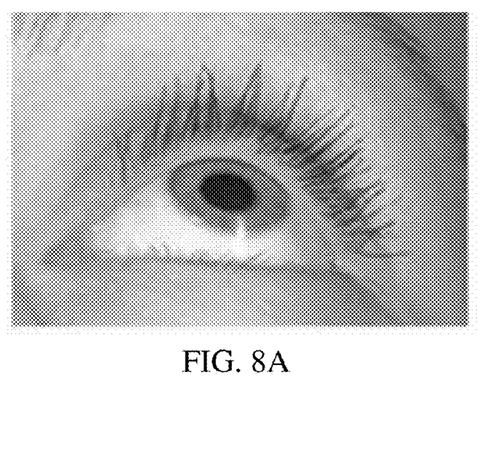
FIG. 8A-8B are photographs that illustrate the eyelashes of a test subject after application of mascara with a twisted wire brush.
Figure 8B:
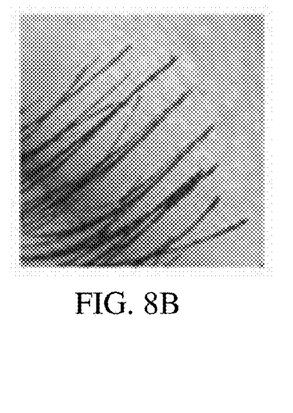
Figure 9A:
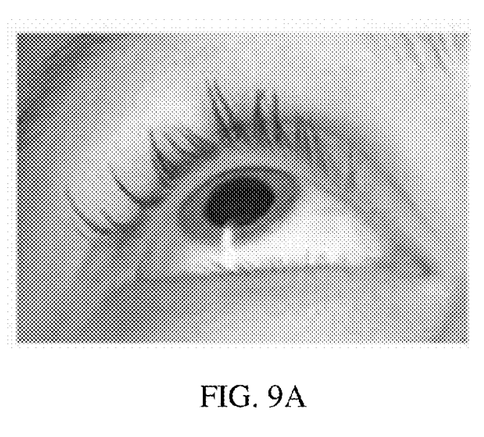
FIG. 9A-9B are photographs that illustrate the eyelashes of a test subject 24 hours after application of mascara with a molded plastic brush.
Figure 9B:
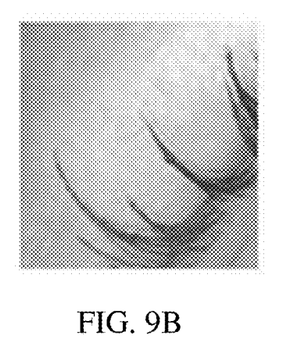
Figure 10A:
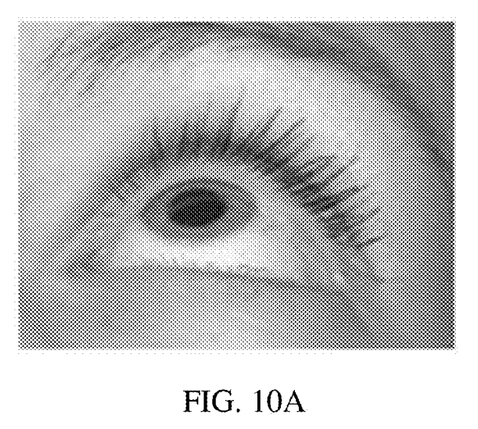
FIGS. 10A-10B are photographs that illustrate the eyelashes of a test subject 24 hours after application of mascara with a twisted wire brush.
Figure 10B:
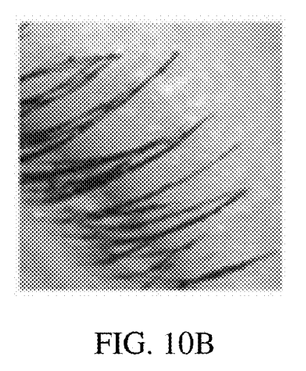

FIGS. 7A-10B illustrate the difference in the separation observed during the consumer test. FIG. 7A shows eyelashes immediately after mascara application with a molded plastic brush. FIG. 7B is a blow up view of the eyelashes in FIG. 7A. FIG. 8A shows eyelashes immediately after mascara application with the twisted-wire brush. FIG. 8B is a blow up view of the eyelashes in FIG. 8B. FIG. 9A shows the eyelashes after 24 hours of mascara application with the molded plastic brush. FIG. 9B is a blow up view of the eyelashes in FIG. 9A. FIG. 10A shows the eyelashes 24 hours after mascara application with the twisted-wire brush. FIG. 10B is a blow up view of the eyelashes in FIG. 10A.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm" Additionally, properties described herein may include one or more ranges of values. It is to be understood that these ranges include every value within the range, even though the individual values in the range may not be expressly disclosed.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for quantitatively determining eyelash clumping, the method comprising:
   a. providing an eyelash substrate comprising an array of eyelashes, each eyelash having a length defined by a base and an opposing tip;
   b. capturing a first image of the eyelashes prior to depositing a mascara for use as a ghost image;
   c. applying an amount of the mascara to the eyelashes;
   d. capturing a second image of the eyelashes with the mascara applied thereto;
   e. analyzing a first portion of second the image to obtain first individual thickness measures for each eyelash disposed in the first portion;
   f. analyzing a second portion of the second image to obtain second individual thickness measures for each eyelash disposed in the second portion;

g. obtaining first average thickness measures from the first individual thickness measures and second average thickness measures from the second individual thickness measures;
h. applying a weighting function to the first and second average thickness measures to generate first and second weighted thickness values; and
i. obtaining a Weighted Average Thickness value from the first and second average thickness measures to provide a quantitative determination of eyelash clumping;
j. wherein the second image of the eyelashes with the mascara applied thereto is superimposed on the ghost image and aligned therewith.

2. The method of claim 1, wherein the weighting function is $Y=0.0675x^2-23.75x+225$, where Y is the weighted thickness value and x is the average thickness measure.

3. The method of claim 1, wherein the image of the eyelashes with the mascara applied thereto is analyzed by using a computer and image analysis software.

4. The method of claim 1, wherein the image of the eyelashes with the mascara applied thereto is cropped after aligning ghost image.

5. The method of claim 1, wherein the image is converted to a black and white binary image that includes white regions and black regions, the black regions corresponding to the eyelashes.

6. The method of claim 5, wherein the first portion and second portions of the image are bar-code images having a height of between 1 and 5 pixels, where 1 pixel is spatially calibrated to represent 10.4 microns.

7. The method of claim 6, wherein the bar-code image is analyzed to determine a thickness of each black region.

8. The method of claim 1, wherein the first and second portions are spaced apart by a predetermined amount.

9. The method of claim 8, wherein the predetermined amount is between 1 and 10 pixels, where 1 pixel is spatially calibrated to represent 10.4 microns.

10. The method of claim 1, wherein the image is captured using a digital single-lens reflex camera with a resolution of at least 7 megapixels.

11. The method of claim 1, wherein the mascara is applied to the eyelashes by a person with a mascara brush.

12. The method of claim 1, wherein the mascara is applied using between 1 and 10 strokes.

13. The method of claim 12, wherein a first weighted average thickness value is determined at 1 stroke or a first number of strokes and a second weighted average thickness value is determined at a second number of strokes, the first number of strokes being less than the second number of strokes.

14. The method of claim 13, wherein the first weighted average thickness value is compared to the second weighted average thickness value to obtain a dump and fix clumping profile for a mascara product.

15. The method of claim 1, further comprising joining the eyelash substrate to a repositioning template.

16. The method of claim 15, further comprising placing the repositioning template in a target image area.

17. The method of claim 1, wherein at least one of the first and second portions extends across the entire array of eyelashes.

18. The method of claim 1, further comprising one or more additional portions extending along the entire length of the eyelashes at predetermined spacing.

* * * * *